United States Patent
Nagamine et al.

(10) Patent No.: US 12,083,461 B2
(45) Date of Patent: Sep. 10, 2024

(54) FILTER MATERIAL FOR REMOVING LEUKOCYTES, LEUKOCYTE REMOVAL FILTER AND METHOD FOR PRODUCING SAME

(71) Applicant: KANEKA CORPORATION, Osaka (JP)

(72) Inventors: Kazuya Nagamine, Settsu (JP); Takayuki Miyamoto, Settsu (JP); Takekazu Maeda, Settsu (JP)

(73) Assignee: KANEKA CORPORATION, Osaka (JP)

( * ) Notice: Subject to any disclaimer, the term of this patent is extended or adjusted under 35 U.S.C. 154(b) by 763 days.

(21) Appl. No.: 17/258,810

(22) PCT Filed: Jul. 9, 2019

(86) PCT No.: PCT/JP2019/027187
§ 371 (c)(1),
(2) Date: Jan. 8, 2021

(87) PCT Pub. No.: WO2020/013193
PCT Pub. Date: Jan. 16, 2020

(65) Prior Publication Data
US 2021/0268415 A1 Sep. 2, 2021

(30) Foreign Application Priority Data
Jul. 13, 2018 (JP) .................. 2018-133398

(51) Int. Cl.
*B01D 39/16* (2006.01)
*A61M 1/02* (2006.01)
(Continued)

(52) U.S. Cl.
CPC ......... *B01D 39/163* (2013.01); *A61M 1/0281* (2013.01); *D04H 3/011* (2013.01);
(Continued)

(58) Field of Classification Search
CPC .......... B01D 39/163; B01D 2239/0421; B01D 2239/0622; B01D 2239/12;
(Continued)

(56) References Cited

U.S. PATENT DOCUMENTS

2018/0154053 A1 6/2018 Shimada et al.
2018/0280844 A1* 10/2018 Shim ...................... D21H 13/24

FOREIGN PATENT DOCUMENTS

JP 3694117 B2 * 9/2005
WO WO 2016/204289 A1 12/2016
WO WO2017055638 * 4/2017

OTHER PUBLICATIONS

English language machine translation of JP3694117B2, 8 pages, No Date.*

(Continued)

*Primary Examiner* — Pranav N Patel
(74) *Attorney, Agent, or Firm* — Birch, Stewart, Kolasch & Birch, LLP

(57) ABSTRACT

A filter material for removing leukocytes including a nonwoven fabric composed of polyester fibers, the nonwoven fabric having a first endothermic peak at a melting point and a second endothermic peak having a maximum in a temperature range from 155° C. to 225° C. in a DSC curve obtained by differential scanning calorimetry (DSC).

13 Claims, 3 Drawing Sheets

(51) Int. Cl.
*D04H 3/011* (2012.01)
*D04H 3/16* (2006.01)

(52) U.S. Cl.
CPC ........... *D04H 3/16* (2013.01); *D10B 2331/04* (2013.01); *D10B 2401/10* (2013.01)

(58) Field of Classification Search
CPC .... B01D 2239/1216; B01D 2239/1233; B01D 2239/1291; A61M 1/0281; A61M 1/3633; D04H 3/011; D04H 3/16; D04H 1/56; D10B 2331/04; D10B 2401/10; C09D 201/00
See application file for complete search history.

(56) References Cited

OTHER PUBLICATIONS

International Search Report, issued in PCT/JP2019/027187, dated Sep. 17, 2019.
Written Opinion of the International Searching Authority, issued in PCT/JP2019/027187, dated Sep. 17, 2019.

* cited by examiner

[Fig. 1]
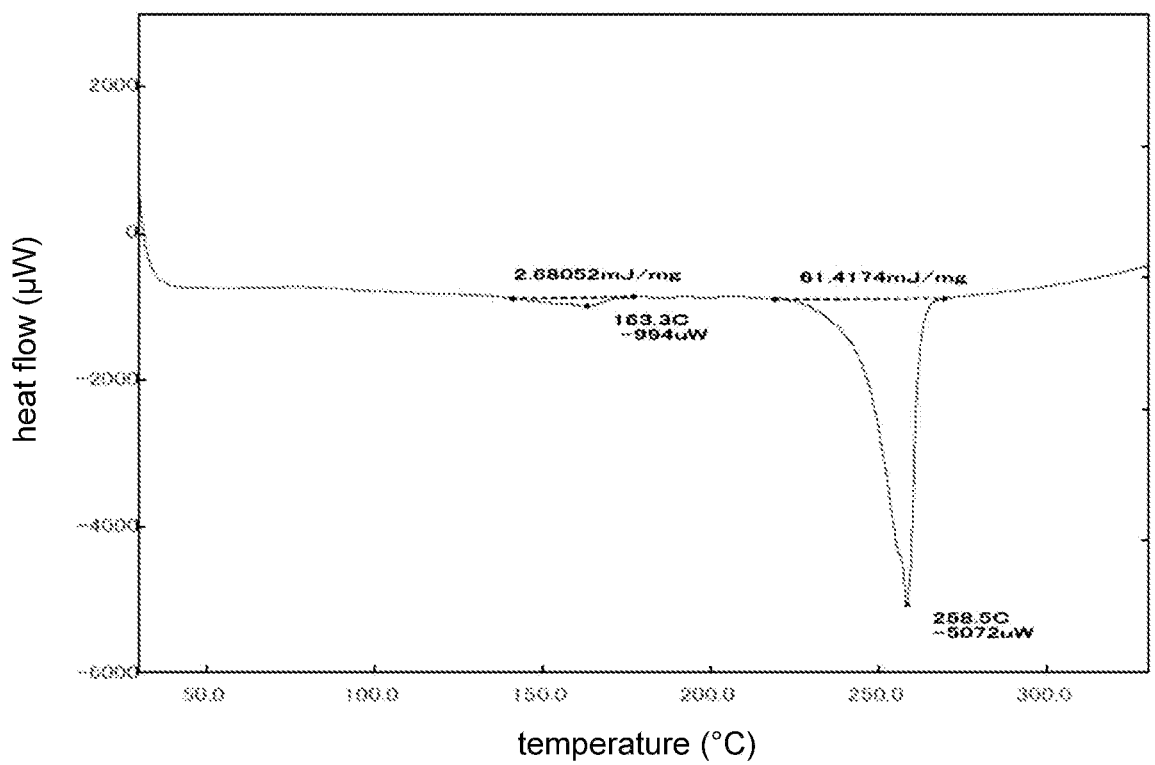
[Fig. 2]
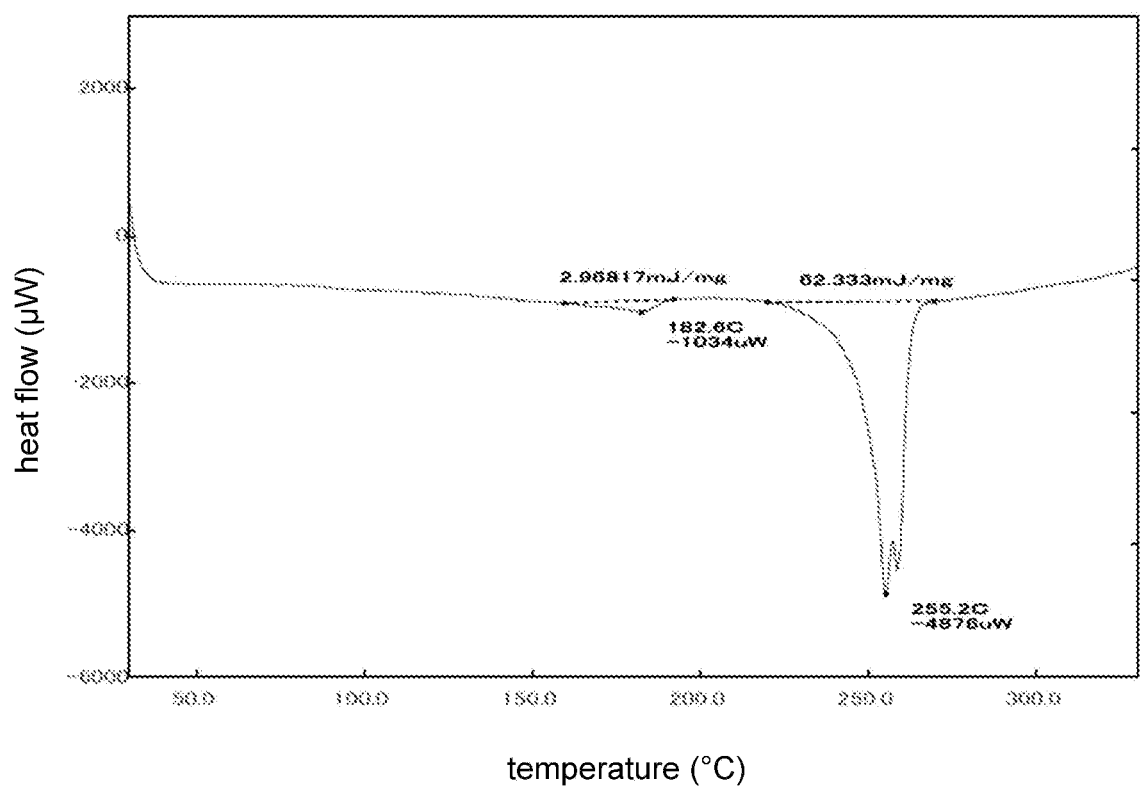

[Fig. 3]
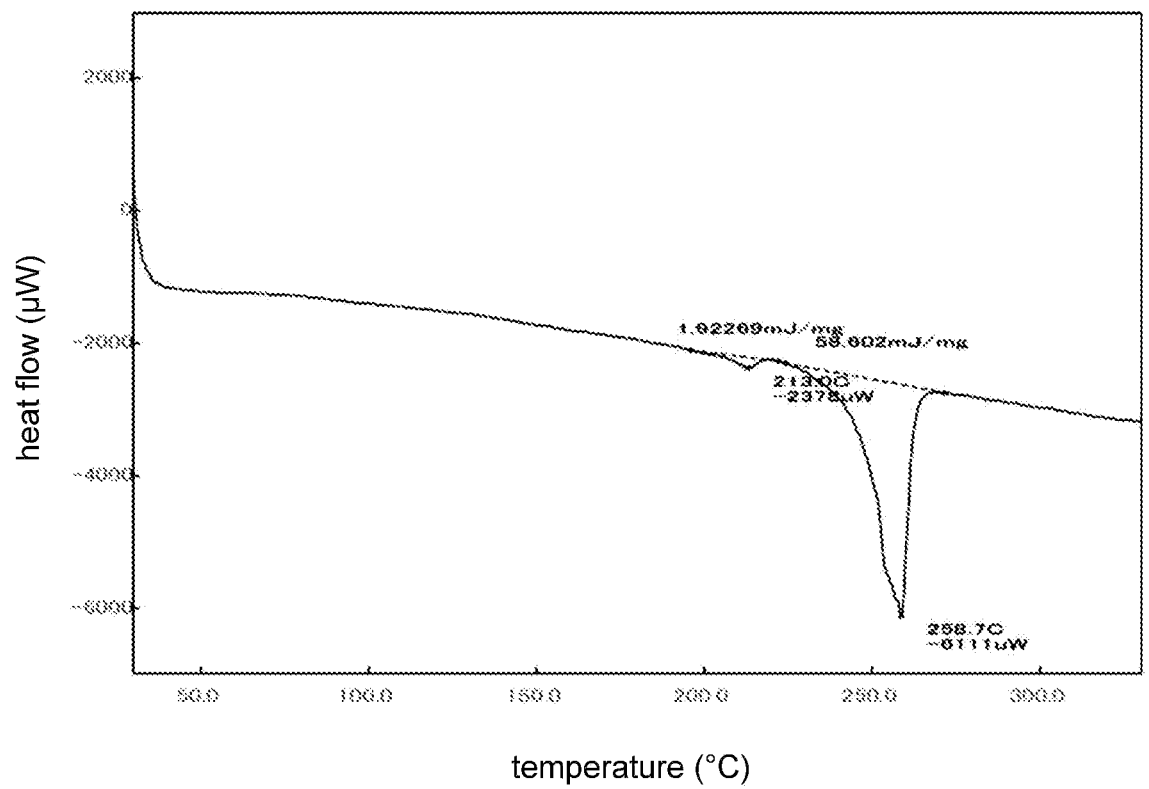
[Fig. 4]
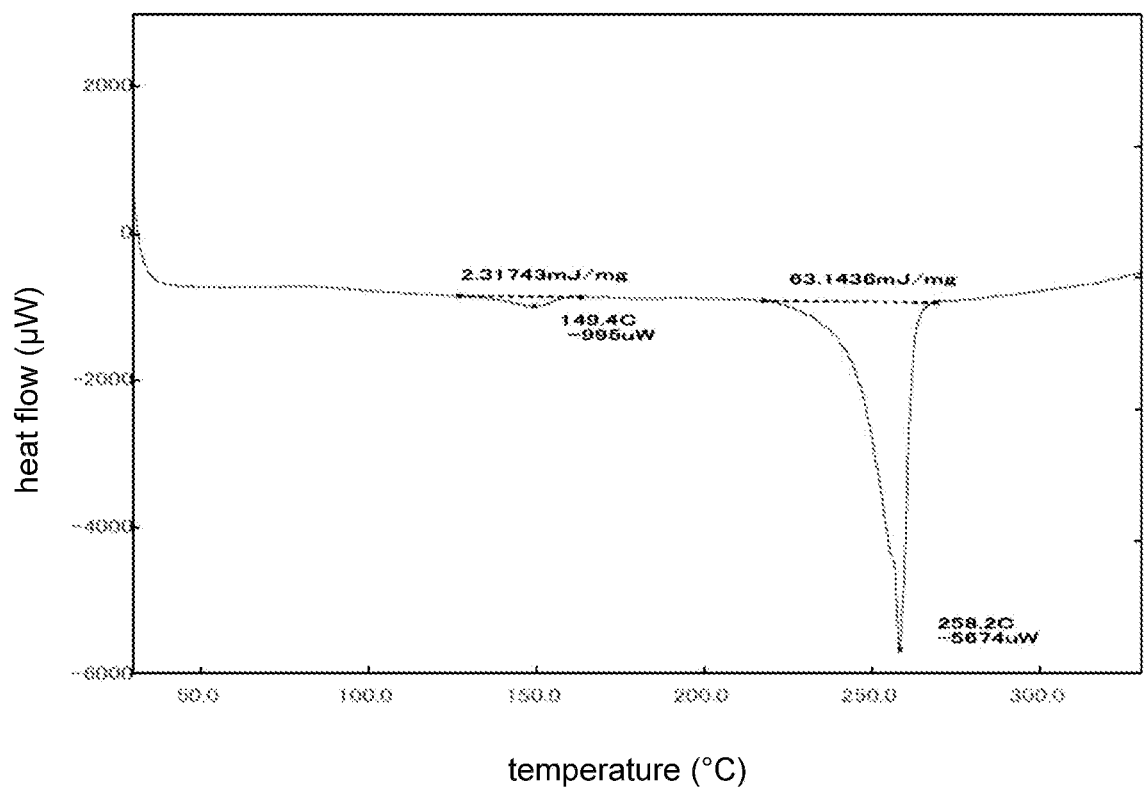

[Fig. 5]
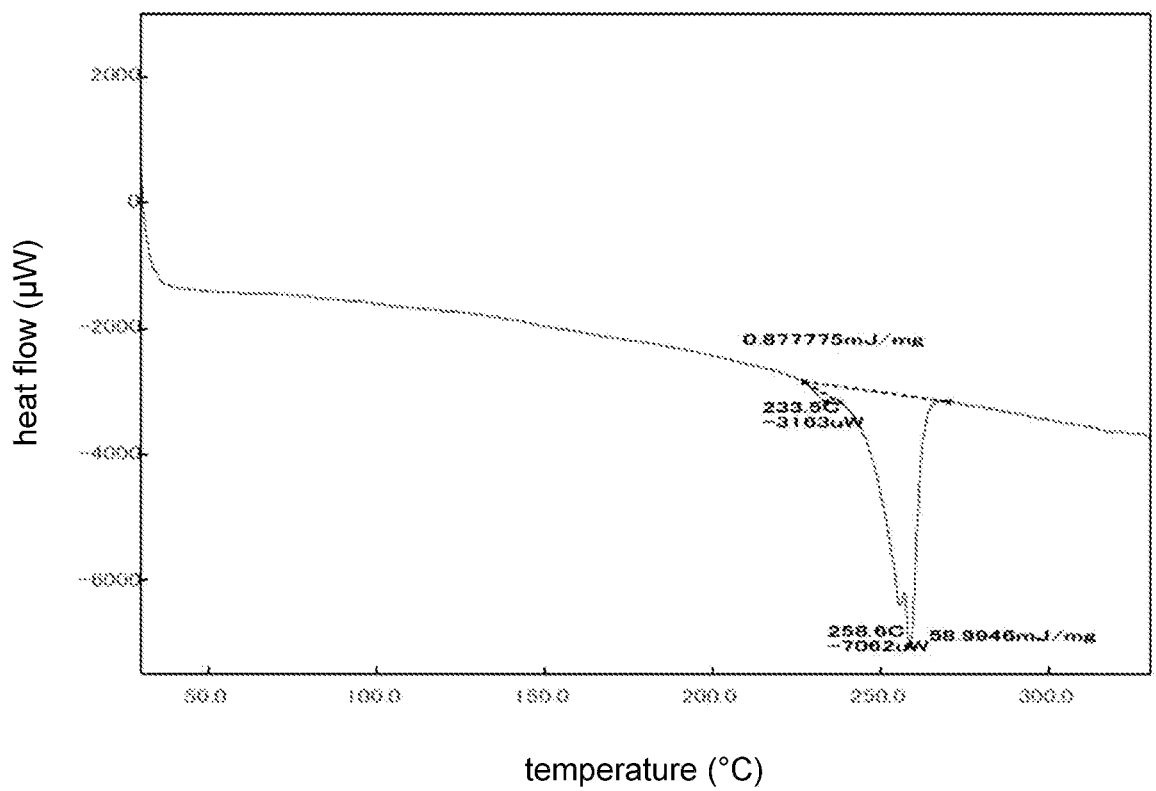
[Fig. 6]
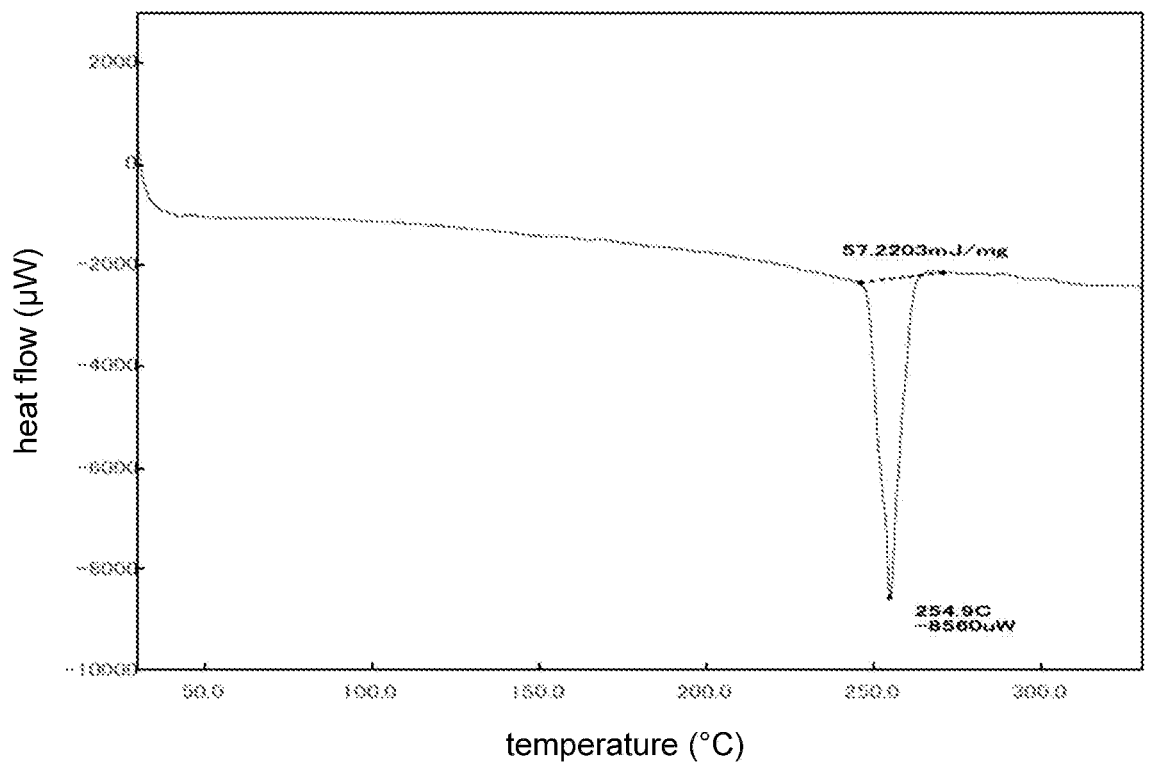

FILTER MATERIAL FOR REMOVING LEUKOCYTES, LEUKOCYTE REMOVAL FILTER AND METHOD FOR PRODUCING SAME

TECHNICAL FIELD

The present invention relates to a filter material for removing leukocytes from blood and the like, a leukocyte removal filter having the filter material, and a method for producing the same.

BACKGROUND ART

A blood product for transfusion is a drug product from which leukocytes are removed before being stored with the purpose of reducing transfusion reactions such as fever and infectious diseases caused by leukocytes. As a method for removing leukocytes from blood and the like, while centrifugation method taking advantage of difference in density of cells and filter method using a porous body as a filtering medium are generally known, the filter method, which is easy-to-operate to achieve high leukocyte removal performance of leukocytes, is widely used. As an example of the filter method for removing leukocytes, a nonwoven fabric is used as a filter material. Various nonwoven fabrics have been developed as the filter material for a leukocyte removal filter, which aims to improve leukocyte removal performance by controlling their thermal properties. For example, Patent Document 1 discloses a leukocyte removal filter having a filter material made of a nonwoven fabric that has a quantity of crystallization heat of an uncrystallized portion of 5 J/g or less before steam heat treatment.

RELATED ART DOCUMENT

Patent Document

Patent Document 1: WO2016/204289

SUMMARY OF THE INVENTION

Problems to be Solved by the Invention

A nonwoven fabric used for a leukocyte removal filter needs to be made of ultrafine fibers having a diameter of about 10 μm or not more than 10 μm in order to form pores which size is in the same range of or smaller than blood cells and the like. In addition, in the production of the leukocyte removal filter, sterilization is required to kill microbes such as pathogens that are accidentally introduced in the producing process, and for this purpose, steam sterilization is commonly used. Therefore, the nonwoven fabric made of ultrafine fibers, which is used for the leukocyte removal filter, is affected by heat of the steam sterilization, and then is to be used as a filter material. According to a study by the present inventors about the leukocyte removal filter disclosed in the Patent Document 1, it has been discovered that thermal effect of the steam sterilization produces a change in thermal properties of the nonwoven fabric of the filter material, and as a result, the leukocyte removal filter after being steam sterilized sometimes fails to obtain desirable leukocyte removal performance.

The present invention has been achieved to solve problems including the above-mentioned problem, the purpose of which is to offer a filter material for removing leukocytes and a leukocyte removal filter having superior leukocyte removal performance.

Means for Solving the Problems

Present inventors carried out intensive studies to solve the aforementioned problems, and eventually completed the present invention. Namely, the present invention is as follows.

[1] A filter material for removing leukocytes comprising: a nonwoven fabric composed of polyester fibers,
the nonwoven fabric having a first endothermic peak at a melting point and a second endothermic peak having a maximum in a temperature range from 155° C. to 225° C. in a DSC curve obtained by differential scanning calorimetry (DSC).

[2] The filter material according to [1], wherein the nonwoven fabric has an elongation in at least one direction of 15% or more.

[3] The filter material according to [2], wherein the nonwoven fabric has the elongation of 20% or more.

[4] The filter material according to any one of [1] to [3], wherein constituent fibers of the nonwoven fabric contain 95% by mass or more of polyester fibers.

[5] The filter material according to any one of [1] to [4], wherein the polyester fibers are polyethylene terephthalate fibers.

[6] The filter material according to any one of [1] to [5], wherein constituent fibers of the nonwoven fabric have an average fiber diameter of 3 μm or less.

[7] The filter material according to any one of [1] to [6], wherein the nonwoven fabric is a meltblown nonwoven fabric.

[8] A leukocyte removal filter, comprising the filter material according to any one of [1] to [7] disposed in a filter holder.

[9] A method for producing a leukocyte removal filter having a filter holder in which a filter material having a nonwoven fabric composed of polyester fibers is disposed, the method comprising:
a) heat treating a nonwoven fabric composed of polyester fibers in a fixed state at a temperature of 155° C. to 225° C.;
b) applying a hydrophilic coating to the nonwoven fabric heat treated in step a), so as to obtain a hydrophilic-coated nonwoven fabric;
c) disposing a filter material including the hydrophilic-coated nonwoven fabric in a filter holder, and sealing the filter holder; and
d) steam sterilizing the filter material disposed in the filter holder at a temperature of 100° C. to 130° C.

[10] The method for manufacturing a leukocyte removal filter according to [9], wherein the polyester fibers are polyethylene terephthalate fibers.

[11] The method for manufacturing a leukocyte removal filter according to [9] or [10], wherein an average fiber diameter of constituent fibers of the nonwoven fabric is 3 μm or less.

Effects of the Invention

The filter material for removing leukocytes and the leukocyte removal filter of the present invention have superior leukocyte removal performance. The filter material for removing leukocytes and the leukocyte removal filter of the present invention can achieve steady high performance even after, for example, the steam sterilization.

BRIEF DESCRIPTION OF THE DRAWINGS

FIG. 1 is a measured DSC data chart of a nonwoven fabric of the filter produced in Preparation Example 1.

FIG. 2 is a measured DSC data chart of a nonwoven fabric of the filter produced in Preparation Example 2.

FIG. 3 is a measured DSC data chart of a nonwoven fabric of the filter produced in Preparation Example 3.

FIG. 4 is a measured DSC data chart of a nonwoven fabric of the filter produced in Preparation Example 4.

FIG. 5 is a measured DSC data chart of a nonwoven fabric of the filter produced in Preparation Example 5.

FIG. 6 is a measured DSC data chart of a nonwoven fabric of the filter produced in Preparation Example 6.

MODE FOR CARRYING OUT THE INVENTION

Hereinafter, the present invention will be described in detail. The present invention is not limited by the following embodiments, and can be carried out with modifications, as appropriate, within the scope of the object of the present invention.

In embodiments of the present invention, a filter material of a leukocyte removal filter has a nonwoven fabric composed of polyester fibers, and the nonwoven fabric has a first endothermic peak at a melting point and a second endothermic peak having a maximum in a temperature range from 155° C. to 225° C. in a DSC curve obtained by differential scanning calorimetry (DSC). Such a configuration of the filter material of the present invention makes the filter material show extremely high leukocyte removal performance. In addition, when the filter material and the leukocyte removal filter are produced, it can also reduce changes in thermal properties of the nonwoven fabric of the filter material before and after steam sterilization, which makes it possible for the filter material having high leukocyte removal performance to be easily produced.

Targets of filtration with the filter material is leukocyte-containing liquid. The leukocyte-containing liquid includes, for example, whole blood, bone marrow, umbilical blood, menstrual blood, a tissue extract, and a crude separated product thereof. Animal species as a source of the leukocyte-containing liquid are not particularly limited, and are preferably mammals including a human, cow, mouse, rat, pig, monkey, dog, and cat.

The nonwoven fabric constituting the filter material may be any nonwoven fabric composed of at least polyester fibers, and preferably the polyester fibers are included as a major component of constituent fibers of the nonwoven fabric. Preferably, the constituent fibers of the nonwoven fabric of the filter material contain 75% by mass or more of polyester fibers, more preferably 85% by mass or more, and even more preferably 95% by mass or more.

Polyester constituting the polyester fibers is exemplified by polyethylene terephthalate, polytrimethylene terephthalate, polybutylene terephthalate, polyethylene naphthalate, polybutylene naphthalate, and the like. Among them, polyethylene terephthalate or polybutylene terephthalate is preferably used, and more preferably polyethylene terephthalate is used. Accordingly, as the polyester fibers constituting the nonwoven fabric, polyethylene terephthalate fibers or polybutylene terephthalate fibers are preferably used, and more preferably polyethylene terephthalate fibers are used. In this case, the constituent fibers of the nonwoven fabric contain 75% by mass or more of polyethylene terephthalate fibers or polybutylene terephthalate fibers, more preferably 85% by mass or more, and even more preferably 95% by mass or more.

Types of the nonwoven fabric used for the filter material are not particularly limited, and the nonwoven fabric may be produced by either wet methods or dry methods. From the viewpoint that a nonwoven fabric made of fibers having smaller fiber diameter is obtained, a nonwoven fabric formed by melt blowing method, flash spinning method, or papermaking method is preferable, and the melt blowing method is more preferable. Producing the nonwoven fabric by the melt blowing method can make it easy for a fiber diameter, a basis weight, and the average porous diameter of the filter material to be arbitrarily adjusted. Accordingly, the nonwoven fabric of the filter material is preferably a melt-blown nonwoven fabric.

An example of methods for producing a nonwoven fabric by the melt blowing method will be described. Molten polymer melt in an extruder is filtrated by an appropriate filter, and then introduced to a molten polymer introduction part of a melt blowing die, which is subsequently discharged from an orifice-shaped nozzle. At the same time, heated gas introduced to a heated gas introduction part is introduced to a heated gas ejection slit formed by melt blowing die trip, from which the gas is ejected to break up the discharged molten polymer and form ultrafine fibers, and the ultrafine fibers are laminated to form a nonwoven fabric. In the process, spinning conditions including resin viscosity, a melting temperature, a throughput per hole, a heated gas temperature, a heated gas pressure, a distance between a spinneret and a collecting net can be appropriately selected and adjusted in accordance with the type of resin to obtain a nonwoven fabric having a desired fiber diameter and basis weight, and to control fiber orientation and fiber dispersibility. In addition, by a thermal pressing process, the thickness and the average porous diameter of the nonwoven fabric may be controlled.

The nonwoven fabric of the filter material has a first endothermic peak at a melting point and a second endothermic peak having a maximum in the temperature range from 155° C. to 225° C. in a DSC curve obtained by differential scanning calorimetry (DSC). The first endothermic peak is derived from the melting point of the constituent fibers of the nonwoven fabric. Polyethylene terephthalate fibers generally have the endothermic peak derived from the melting point in the temperature range from 250° C. to 260° C., and polybutylene terephthalate fibers generally have the endothermic peak derived from the melting point in the temperature range from 220° C. to 230° C. The second endothermic peak is considered to be derived from a crystal structure that is different in stability (for example, size and structure) from the crystal structure at the melting point. The second endothermic peak of the nonwoven fabric of the filter material suggests that the constituent fibers of the nonwoven fabric (especially, polyester fibers) have more than one crystal structure. From the study of the relation to filtering performance of the filter material focusing on the second endothermic peak by the present inventors, it has been discovered that in the case where the maximum of the second endothermic peak is present in the temperature range from 155° C. to 225° C., the filter material can remove leukocytes, which cause various non-hemolytic transfusion reactions when remaining in a blood product, at high removal rate, and at the same time collect erythrocyte in high yield. In addition, it has been also discovered that appropriately adjusting the maximum of the second endothermic peak enables another crystal structure than the crystal structure at the melting point to obtain a certain level of stability.

The differential scanning calorimetry is conducted in the following way. The nonwoven fabric is taken out from the filter material. About 4.5 to 5.5 mg of the nonwoven fabric is placed in an aluminum pan (diameter: 5 mm), and measured with a differential scanning calorimeter (EXSTAR6000 DSC6200R, manufactured by Seiko Instruments Inc.) under a nitrogen atmosphere under the condition where the onset temperature is 30° C., the end temperature is 370° C., and the ramp rate is 10° C./min to obtain a DSC curve.

In order to obtain the aforementioned nonwoven fabric having the maximum of the second endothermic peak in the temperature range from 155° C. to 225° C., it is necessary to heat treat the nonwoven fabric at a predetermined temperature. The lower limit of the heat treatment temperature is preferably 155° C., and the upper limit of the heat treatment temperature is preferably 225° C. Duration time of the heat treatment, which depends on the fiber diameter of the nonwoven fabric, is appropriately determined preferably between 30 seconds and one hour.

The average fiber diameter of the constituent fibers of the nonwoven fabric of the filter material is, from the viewpoint of improving leukocyte removal performance of the filter material, preferably 10 μm or less, more preferably 5 μm or less, even more preferably 3 μm or less, and still even more preferably 2 μm or less. On the other hand, the average fiber diameter of the constituent fibers of the nonwoven fabric of the filter material is preferably 0.3 μm or more. The fiber diameter of the constituent fiber in the above range enables the nonwoven fabric to be stably produced, and can prevent viscous resistance from getting too high when blood is filtered with the filter material. The average fiber diameter is determined in accordance with the following process. A part of the filter material is sampled, from which 100 or more of fibers are arbitrarily selected. Based on the scanning electron microscope photograph, the diameter of each of the 100 or more of arbitrarily selected fibers is measured to obtain the average fiber diameter by number averaging.

The nonwoven fabric of the filter material preferably has the lower limit of the average porous diameter of 1 μm, and more preferably 2 μm. The average porous diameter of 1 μm or more makes it easier for filtration time to be reduced. On the other hand, the upper limit of the average porous diameter is preferably 10 μm, and more preferably 6 μm. The average porous diameter of 10 μm or less makes it easier for the leukocyte removal performance to be secured. The average porous diameter of the nonwoven fabric of the filter material means a mean flow pore size measured with a permporometer (manufactured by Porous Materials Inc).

The nonwoven fabric of the filter material preferably has the lower limit of a basis weight of 5 g/m$^2$, and more preferably 20 g/m$^2$. The basis weight of 5 g/m$^2$ or more makes it easier for a tensile strength of the filter material to be secured. On the other hand, the upper limit of the basis weight of the nonwoven fabric of the filter material is preferably 80 g/m$^2$, and more preferably 60 g/m$^2$. The basis weight of 80 g/m$^2$ or less prevent flow resistance from excessively increasing when filtering, which makes it easier for filtering time to be shortened. The basis weight means a value obtained by measuring weight (g) per unit area (1 m$^2$) of the nonwoven fabric.

The nonwoven fabric of the filter material preferably has an elongation in at least one direction of 15% or more, and more preferably 20% or more. This makes it unlikely for the nonwoven fabric to be broken at the time of manufacturing of the filter material or filtering with the filter material. The nonwoven fabric preferably has a maximum elongation of 15% or more or 20% or more. For example, at least the largest value among values of elongation when the nonwoven fabric is elongated in four direction each of which is angularly different by 450 may be 15% or more or 20% or more. Note that a nonwoven fabric generally has a maximum elongation in the transverse direction (TD) that is orthogonal to the machine direction (MD) in which the nonwoven fabric is conveyed (wound) when produced. The upper limit of the elongation of the nonwoven fabric is not particularly limited, and for example, the maximum elongation is preferably 50% or less, and more preferably 35% or less.

The elongation of the nonwoven fabric is measured as follows. The nonwoven fabric is taken from the filter material, from which a test piece whose size is 8 mm wide and 40 mm long is cut out. Using a universal testing machine (RTG-1210, manufactured by A&D Company, Limited), both ends of the test piece are fixed by chucks, the distance between which is 20 mm, and the chucks are pulled away from each other to elongate the test piece at an elongation rate of 20 mm/min. The distance between the chucks when the test piece is broken is measured to obtain the elongation in accordance with the following formula: elongation (%)= ((distance between the chucks when the test piece is broken-20)/20)×100.

The nonwoven fabric of the filter material may be surface treated. For example, the surface of the fibers is preferably reformed by graft polymerization, polymer coating, chemical treatment including alkali treatment and acid treatment, plasma treatment, and the like. Of these, the nonwoven fabric is preferably coated with a hydrophilic coating, which can increase the affinity of the filter material with blood and the like to improve wettability.

The hydrophilic coating is preferably polymer coating. The polymer coating can easily reform the surface of the fibers into a favorable structure. For the polymer coating, any hydrophilic polymer may be used, unless it has particularly large burden on blood component. The hydrophilic polymer includes a polymer having hydrophilic functional groups such as hydroxyl group, amino group, carboxyl group, sulfonic acid group, carbonyl group, and sulfonyl group. Of these, polyvinylpyrrolidone and copolymer of a monomer such as hydroxyethyl (meth)acrylate and dimethylaminoethyl (meth)acrylate or diethylaminoethyl (meth)acrylate, which have a basic functional group, are especially preferable, because they can improve wettability of the nonwoven fabric by hydrophilization of the surface of the fibers, and also improve performance of trapping blood cells including leukocyte by introducing a charged functional group.

Methods of polymer coating may include any method without limitation as long as it does not excessively fill fine pores of the filter material, that is the fiber gaps of the nonwoven fabric, and it can uniformly coat the surface of the nonwoven fabric in a certain range. For example, methods of polymer coating are exemplified by a method where the nonwoven fabric is immersed in a solution in which polymer is dissolved, a method where a solution in which polymer is dissolved is sprayed to the nonwoven fabric, and a method where a solution in which polymer is dissolved is applied and transferred to the nonwoven fabric with a gravure roll and the like. Of these, the method where the nonwoven fabric is immersed in a solution in which polymer is dissolved is preferable because it is excellent in continuous productivity and small in cost.

A solvent in which the polymer is dissolved is not particularly limited unless it does not significantly dissolve the nonwoven fabric of the filter material, and exemplified by amides such as N,N-dimethylformamide and N,N-dimethylacetamide; sulfoxides such as dimethylsulfoxide; alcohols such as methanol, ethanol, propanol, butanol; ketones such as acetone and methyl ethyl ketone; esters such as methyl acetate and ethyl acetate; hydrocarbons such as toluene and cyclohexane; halogenated hydrocarbons such as chloroform and dichloromethane; water; and a mixture of two or more of these solvents. Of these, alcohols such as methanol, ethanol, propanol, and butanol is preferable, and especially preferably, methanol and ethanol.

The filter material of the present embodiment may have one aforementioned nonwoven fabric, or may have a laminate of two or more of the nonwoven fabric. Or the filter material of the present embodiment may have arbitrary nonwoven fabric laminated on the aforementioned nonwoven fabric. Laminating two or more of nonwoven fabrics to form the filter material can improve removal performance of leukocyte. In the case where two or more of nonwoven fabrics are laminated, two or more of nonwoven fabrics may be placed to be laminated to the direction of flow of leukocyte-containing liquid which is to be filtered. In the case where two or more of nonwoven fabrics are laminated, the number of laminated nonwoven fabrics is preferably 10 or more, and more preferably 20 or more. On the other hand, the number of laminated nonwoven fabrics is preferably 60 or less, and more preferably 50 or less from a viewpoint of reducing filtering time.

Next, a leukocyte removal filter of the present invention will be described. The leukocyte removal filter of the present invention is such that the filter material of the present embodiments is disposed in a filter holder. In the filter holder, one filter material may be disposed, or two or more filter materials may be disposed. In addition, different kind of filter material may be included on the upstream side or the downstream side. For example, by placing a filter material having larger basis weight and larger average pore size than the nonwoven fabric of the present embodiments to behave as a prefilter, effects such as reduced filter time can be expected. Furthermore, since leukocyte-containing liquid often includes a bad influence on good performance of the filter material such as micro aggregation substances, these substances are preferably removed with the prefilter. As the prefilter, for example, a continuous porous body having an average pore diameter of 20 μm to 200 μm is preferably used.

The leukocyte removal filter has the nonwoven fabric of the present embodiments as the filter material, and is preferably such that the filter material is disposed in the filter holder having a liquid inlet and a liquid outlet. The filter holder may have an arbitrary form such as a sphere, a container, a cassette, a bag, a tube, and a column, and for example, a cylindrical form having a content of about 0.1 mL to 1000 mL and a diameter of about 0.1 cm to 15 cm, or a quadrangular prism form a side of which is square or rectangular having a side length of about 0.1 cm to 20 cm and a thickness of which is about 0.1 cm to 5 cm is preferable. At least a part of the filter holder is preferably transparent or translucent, which enables visual confirmation of progress of filtration.

The leukocyte removal filter having the filter material of the present embodiments can be produced, for example, as follows. That is, it includes a) heat treating a nonwoven fabric composed of polyester fibers in a fixed state at a temperature of 155° C. to 225° C.; b) applying a hydrophilic coating to the nonwoven fabric heat treated in the step a), so as to obtain a hydrophilic-coated nonwoven fabric; c) disposing a filter material including the hydrophilic-coated nonwoven fabric in a filter holder, and sealing the filter holder; and d) steam sterilizing the filter material disposed in the filter holder at a temperature of 100° C. to 130° C. to produce the leukocyte removal filter equipped with the filter material having the nonwoven fabric composed of polyester fibers in the filter holder.

In the heat treatment of the process a), the nonwoven fabric composed of polyester fibers is heat treated in a fixed state at a temperature of 155° C. to 225° C. For details of the nonwoven fabric composed of polyester fibers, the above description is referred to. By heat treating the nonwoven fabric composed of polyester fibers at a temperature of 155° C. to 225° C., the nonwoven fabric representing the maximum value of endothermic peak in a temperature range from 155° C. to 225° C. in a DSC curve.

In the heat treatment process, the nonwoven fabric is preferably treated in a fixed state from a viewpoint of preventing the nonwoven fabric from significantly shrinking in size when heat treated. For example, to make the nonwoven fabric in a fixed state, the nonwoven fabric is preferably fixed to the uniaxial direction or the biaxial direction of the longitudinal and the width direction of the plane of the nonwoven fabric, or fixed in the perpendicular axis to the plane of the nonwoven fabric. To fix the nonwoven fabric to the longitudinal and the width direction of the plane of the nonwoven fabric, for example, end portion of the nonwoven fabric may be fixed with a fixture such as a metal frame. To fix the nonwoven fabric in the perpendicular axis to the plane of the nonwoven fabric, for example, the nonwoven fabric may be heat treated in a condition where the nonwoven fabric is configured to be stacked in a roll.

In the coating process of the process b), a hydrophilic coating is applied to the nonwoven fabric that has been heat treated. For details of the hydrophilic coating, the above description is referred to. The coating process is preferably performed after the nonwoven fabric is cooled to ordinary temperatures subsequent to the heat treatment process. For example, the nonwoven fabric that has been heat treated is preferably cooled for over 5 minutes.

In the assembling process of the process c), a filter material including the hydrophilic-coated nonwoven fabric is disposed in a filter holder, and the filter holder is sealed to produce a filter unit. For details of the filter holder and the disposition of the filter material, the above description is referred to. In the assembly process, the filter material can be shut from the outside by sealing the filter holder.

In the sterilizing process of the process d), the filter material disposed in the filter holder is steam sterilized at a temperature of 100° C. to 130° C. By sterilizing the filter material in the sterilizing process, the filter material can be kept in a sanitary condition until the leukocyte removal filter begins to be used. The steam sterilization can be performed by disposing the filter material to be sterilized in the filter holder in a sealed condition, and heating the filter material with saturated water vapor at 100° C. or higher. The sterilization may be performed at about 100° C. to 130° C. for about 20 minutes to 60 minutes, for example, at 121° C. for 20 minutes or at 118° C. for 40 minutes.

In accordance with the aforementioned method for producing the leukocyte removal filter, the filter material after the heat treatment shows a high rate of leukocyte removal, and the filter material after the sterilization process still maintains performance of the filter material to show a high rate of leukocyte removal. It means that since thermal properties of the filter material is not likely to change due to thermal effect of the steam sterilization, the leukocyte removal filter exhibiting extremely high leukocyte removal performance can be easily produced.

The present application claims priority based on Japanese Patent Application No. 2018-133398 filed on Jul. 13, 2018. All the contents described in Japanese Patent Application No. 2018-133398 filed on Jul. 13, 2018 are incorporated herein by reference.

EXAMPLES

Hereinafter, the present invention will be described in detail with reference to examples, however, the present invention is not limited to only the following examples.

(1) Production Examples of Filter (1-1) Production Example 1

Using polyethylene terephthalate (PET), a nonwoven fabric composed of polyethylene terephthalate fibers was produced by melt blowing method. The average fiber diameter of the nonwoven fabric was 1.52 μm, the basis weight of the nonwoven fabric was 40 g/m$^2$, the thickness of the nonwoven fabric was 0.42 mm, and the average pore diameter was 3.30 μm. The obtained nonwoven fabric was fixed to the biaxial direction of the longitudinal and the width direction of the plane of the nonwoven fabric with a metal frame, which was placed in a dryer (PH202, manufactured by ESPEC Corporation) heated to 160° C. to be heat treated for 3 minutes. Subsequently, the nonwoven fabric was taken out from the dryer, and naturally cooled at a room temperature to obtain a heat treated nonwoven fabric.

Separately from the above process, a coating solution was prepared as follows. First, 2-hydroxyethyl methacrylate and 2-(dimethylamino)ethyl methacrylate were added to graded ethanol such that the concentration of 2-hydroxyethyl methacrylate was to be 0.95 mol/L, the concentration of 2-(dimethylamino)ethyl methacrylate was to be 0.05 mol/L, and the total amount was to be 300 mL, which was polymerized at 45° C. for 15 hours under a nitrogen atmosphere after 2-2'-azobis(2,4-dimethylvaleronitrile) was added as a polymeric initiator such that the concentration was to be 0.005 mol/L, and subsequently poured to excess n-hexane to deposit a polymer, which was collected. The obtained polymer was dissolved in ethanol again. It was poured to n-hexane to deposit a polymer, which was dried at 75° C. for 4 hours to obtain a copolymer consisting of 2-hydroxyethyl methacrylate and N,N-(dimethylamino)ethyl methacrylate (hereinafter, referred to as "HEDM"). The HEDM was dissolved in ethanol such that the concentration of the HEDM was to be 1.0 g/L to obtain a HEDM coating solution.

The heat treated nonwoven fabric was soaked in the HEDM coating solution prepared as described above at 20° C. for a few tens of seconds to 5 minutes, which was subsequently placed in a stainless basket and dried at 80° C. for 5 minutes to obtain a coated nonwoven fabric. The coated nonwoven fabric obtained as described above was cut out into squares of 7.2 cm×7.2 cm, 32 sheets of which was placed in a square housing (filter holder) of 7.2 cm×7.2 cm×0.85 cm (thickness) to produce a filter unit. An inlet of the filter unit and a blood bag were connected with a tube made of vinyl chloride having a length of 60 cm (outer diameter: 5 mm; inner diameter: 3 mm), and the tube was sealed with a clamp. The obtained filter unit was placed in a steam sterilizer (HG-50, manufactured by Hirayama Manufacturing Corporation) to be steam sterilized at 121° C. for 20 minutes, thereby a leukocyte removal filter equipped with a filter material having the coated PET nonwoven fabric. The filter obtained in Production example 1 is referred to as "filter 1".

(1-2) Production Example 2

Except changing the heat treatment temperature from 160° C. to 180° C. in Production example 1, a leukocyte removal filter was produced in the same manner as Production example 1. The filter obtained in Production example 2 is referred to as "filter 2".

(1-3) Production Example 3

Except changing the heat treatment temperature from 160° C. to 220° C. in Production example 1, a leukocyte removal filter was produced in the same manner as Production example 1. The filter obtained in Production example 3 is referred to as "filter 3".

(1-4) Production Example 4

Except changing the heat treatment temperature from 160° C. to 140° C. in Production example 1, a leukocyte removal filter was produced in the same manner as Production example 1. The filter obtained in Production example 4 is referred to as "filter 4".

(1-5) Production Example 5

Except changing the heat treatment temperature from 160° C. to 230° C. in Production example 1, a leukocyte removal filter was produced in the same manner as Production example 1. The filter obtained in Production example 5 is referred to as "filter 5".

(1-6) Production Example 6

Except changing the heat treatment temperature from 160° C. to 250° C. and the heat treatment time from 3 minutes to 10 minutes in Production example 1, a leukocyte removal filter was produced in the same manner as Production example 1. The filter obtained in Production example 6 is referred to as "filter 6".

(2) Evaluation Method (2-1) Evaluation of Filtering Performance

Into a blood bag (blood bag CPD, manufactured by Terumo Corporation; composition: sodium citrate hydrate 2.63 w/v %, citric acid hydrate 0.327 w/v %, glucose 2.32 w/v %, sodium dihydrogen phosphate 0.251 w/v %) containing 56 mL of anticoagulant CPD liquid, 400 mL of bovine whole blood was collected, which was mixed to prepare a blood sample. The temperature of the blood sample was set to 4° C. using a constant-temperature bath, and then 456 mL of the blood sample in the blood bag was filtered with each filter obtained in the above Production examples by use of gravity (fall length: 60 cm), and filtered blood was collected to a receiver. The length of time it took for the blood bag to become empty from the beginning of filtering was measured to determine filtering time.

Concentration of leukocyte and concentration of erythrocyte in the blood sample before filtering (referred to as "before-filtered blood") and in the filtered blood were measured. The concentration of leukocyte was measured with a flow cytometer LeucoCOUNT kit and FACSCalibur (both were manufactured by Becton, Dickinson and Company) by flow cytometry method, and the concentration of erythrocyte was measured with a blood counter (K-4500, manufactured by Sysmex Corporation). The rate of leukocyte removal (−Log) and the rate of erythrocyte recovery (%) was calculated in accordance with the following formulas. In the following formulas, "a" is the concentration of leukocyte of the before-filtered blood, "b" is the concentration of leukocyte of the filtered blood, "c" is the concentration of erythrocyte of the before-filtered blood, and "d" is the concentration of erythrocyte of the filtered blood. The results of the evaluation of each filter is shown in Table 1.

Rate of leukocyte removal=−Log($b/a$)

Rate of erythrocyte recovery (%)=($d/c$)×100

(2-2) DSC Measurement

The nonwoven fabric, which was the filter material, was taken out from each filter produced in the above Production examples. Using a differential scanning calorimeter (EXSTAR6000 DSC6200R, manufactured by Seiko Instruments Inc.), 4.5 to 5.5 mg of the nonwoven fabric that had been taken from each filter was placed in an aluminum pan (diameter: 5 mm), and measured under a nitrogen atmosphere under the condition where the onset temperature was 30° C., the end temperature was 370° C., and the ramp rate was 10° C./min to obtain a DSC curve. The DSC curves of each filter obtained in the above Production examples are shown in FIG. 1 to FIG. 6, and a temperature of the first endothermic peak, which is a melting point, and a temperature of the maximum at the second endothermic peak are shown in Table 1. Note that in the DSC curves shown in FIG. 1 to FIG. 6, since the endothermic peak appears as a negative peak, the minimum of the DSC curves is to be the maximum of the endothermic peak.

(2-3) Elongation Measurement

The nonwoven fabric, which was the filter material, was taken out from each filter produced in the above Production examples. From the nonwoven fabric that had been taken from each filter, a test piece whose size was 8 mm wide and 40 mm long was cut out. Using a universal testing machine (RTG-1210, manufactured by A&D Company, Limited), both ends of the test piece were fixed by chucks, the distance between which was 20 mm, and the chucks were pulled away from each other to elongate the test piece at an elongation rate of 20 mm/min until the test piece was broken. The distance between the chucks when the test piece was broken was measured to obtain the elongation in accordance with the following formula, and the average of 10 measurements was calculated. The measured elongation of each filter is shown in Table 1.

elongation (%)=((distance between the chucks when the test piece is broken−20)/20)×100.

TABLE 1

|  | Filter 1 | Filter 2 | Filter 3 | Filter 4 | Filter 5 | Filter 6 |
| --- | --- | --- | --- | --- | --- | --- |
| heat treatment temperature (° C.) | 160 | 180 | 220 | 140 | 230 | 250 |
| heat treatment time (minute) | 3 | 3 | 3 | 3 | 3 | 10 |
| temperature at first endothermic peak (° C.) | 258.5 | 255.2 | 258.7 | 258.2 | 258.6 | 254.9 |
| temperature at second endothermic peak (° C.) | 163.3 | 182.6 | 213.0 | 149.4 | 233.5 | N.D. |
| leukocyte removal rate (−log) | >5.27 | >5.27 | >5.27 | 2.51 | N.D. | N.D. |
| erythrocyte recovery rate (%) | 98.1 | 97.8 | 97.9 | 99.0 | N.D. | N.D. |
| filtering time (minute) | 17.1 | 15.2 | 14.7 | 13.2 | N.D. | N.D. |
| elongation in TD direction (%) | 30.3 | 28.0 | 23.5 | 39.9 | 9.1 | 0.9 |

(3) Conclusion

The filters 1 to 3 had a temperature at the maximum of the second endothermic peak in the range of 155° C. to 225° C., and had high leukocyte removal performance and high erythrocyte recovery rate. On the other hand, the filter 4 having a temperature at the maximum of the second endothermic peak of lower than 155° C. had lower leukocyte removal performance than the filters 1 to 3. As for the filter 5 having a temperature at the maximum of the second endothermic peak of higher than 225° C. and the filter 6 not showing the second endothermic peak, the filter material was broken and the filter could not be produced.

The invention claimed is:

1. A filter material for removing leukocytes comprising: a nonwoven fabric composed of polyester fibers, the polyester fibers comprising a polyester material consisting of a polyester composition, the polyester material containing a first crystal structure and a second crystal structure, the polyester fibers having i) a first endothermic peak at a melting point of the polyester composition, the first endothermic peak being derived from the first crystal structure, and ii) a second endothermic peak having a maximum in a temperature range from 155° C. to 225° C., the second endothermic peak being derived from the second crystal structure that is different in stability from the first crystal structure at the melting point in a DSC curve obtained by differential scanning calorimetry (DSC), wherein the nonwoven fabric has an elongation in at least one direction of 15% or more.

2. The filter material according to claim 1, wherein the nonwoven fabric has the elongation of 20% or more.

3. The filter material according to claim 1, wherein constituent fibers of the nonwoven fabric contain 95% by mass or more of polyester fibers.

4. The filter material according to claim 1, wherein the polyester fibers are polyethylene terephthalate fibers.

5. The filter material according to claim 1, wherein constituent fibers of the nonwoven fabric have an average fiber diameter of 3 m or less.

6. The filter material according to claim 1, wherein the nonwoven fabric is a meltblown nonwoven fabric.

7. The filter material according to claim 1, wherein the maximum of the second endothermic peak is lower than the melting point of the polyester composition.

8. The filter material according to claim 1, wherein the polyester fibers have an average fiber diameter of 5 μm or less.

9. The filter material according to claim 1, wherein the nonwoven fabric has been heat treated in a fixed state at a temperature of 155° C. to 225° C., so that the polyester fibers have the first and second endothermic peaks.

10. A leukocyte removal filter, comprising the filter material according to claim 1 disposed in a filter holder.

11. A method for producing a leukocyte removal filter having a filter holder in which a filter material having a nonwoven fabric composed of polyester fibers is disposed, the method comprising:
   a) heat treating a nonwoven fabric composed of polyester fibers in a fixed state at a temperature of 155° C. to 225° C., the polyester fibers comprising a polyester material consisting of a polyester composition;
   b) applying a hydrophilic coating to the nonwoven fabric heat treated in the step a), so as to obtain a hydrophilic-coated nonwoven fabric;
   c) disposing a filter material including the hydrophilic-coated nonwoven fabric in a filter holder, and sealing the filter holder; and
   d) steam sterilizing the filter material disposed in the filter holder at a temperature of 100° C. to 130° C., so that the polyester material contains a first crystal structure and a second crystal structure, the polyester fibers having i) a first endothermic peak at a melting point of the polyester composition, the first endothermic peak being derived from the first crystal structure, and ii) a second endothermic peak having a maximum in a temperature range from 155° C. to 225° C., the second endothermic peak being derived from the second crystal structure that is different in stability from the first crystal structure at the melting point in a DSC curve obtained by differential scanning calorimetry (DSC), wherein the nonwoven fabric has an elongation in at least one direction of 15% or more.

12. The method for manufacturing a leukocyte removal filter according to claim 11, wherein the polyester fibers are polyethylene terephthalate fibers.

13. The method for manufacturing a leukocyte removal filter according to claim 11, wherein an average fiber diameter of the polyester fibers of the nonwoven fabric is 3 μm or less.

* * * * *